(12) United States Patent
Scarborough et al.

(10) Patent No.: US 7,662,133 B2
(45) Date of Patent: Feb. 16, 2010

(54) SPINAL FLUID INTRODUCTION

(75) Inventors: Nelson Scarborough, Germantown, TN (US); John V. Hamilton, Foxborough, MA (US); Andy H. Uchida, Mountain View, CA (US); Ralph I. McNall, Belmont, CA (US); Steven Lepke, Wakefield, MA (US); Peter A. Weissman, North Andover, MA (US)

(73) Assignee: Smith & Nephew, Inc., Memphis, TN (US)

( * ) Notice: Subject to any disclaimer, the term of this patent is extended or adjusted under 35 U.S.C. 154(b) by 345 days.

(21) Appl. No.: 10/782,900

(22) Filed: Feb. 23, 2004

(65) Prior Publication Data

US 2004/0193045 A1    Sep. 30, 2004

Related U.S. Application Data

(60) Provisional application No. 60/448,529, filed on Feb. 21, 2003.

(51) Int. Cl.
*A61M 37/00* (2006.01)
*A61B 5/103* (2006.01)
*A61B 5/117* (2006.01)

(52) U.S. Cl. ....................... 604/154; 600/594

(58) Field of Classification Search ......... 604/151–152, 604/154, 187; 600/430–432, 594
See application file for complete search history.

(56) References Cited

U.S. PATENT DOCUMENTS

| | | | |
|---|---|---|---|
| 3,623,474 A * | 11/1971 | Heilman et al. | 600/432 |
| 3,625,793 A | 12/1971 | Sheridan | |
| 3,878,830 A | 4/1975 | Bicher | |
| RE30,365 E | 8/1980 | Mattler | |
| 4,370,982 A | 2/1983 | Reilly | |
| 4,439,185 A | 3/1984 | Lundquist | |

(Continued)

FOREIGN PATENT DOCUMENTS

EP    1 10 567    6/2001

OTHER PUBLICATIONS

Smith & Nephew Brochure, "Dyonics® Intelijet™ Arthroscopic Fluid Management System Operations Manual," Smith & Nephew, Inc., Endoscopy Division, 2002.

*Primary Examiner*—Kevin C Sirmons
*Assistant Examiner*—Andrew M Gilbert
(74) *Attorney, Agent, or Firm*—Fish & Richardson P.C.

(57) ABSTRACT

A fluid introduction system includes an introducer configured to create a pressure of at least 69 kPa within a spine, and an operator configured to actuate the introducer to introduce fluid into the spine according to a predetermined fluid introduction profile. The system can include a computer readable medium having code for receiving fluid introduction data indicative of a fluid introduction parameter, and for receiving response data indicative of a response of the patient at a time related to a time of the fluid introduction data. A method for introducing fluid includes positioning a first introducer in a first portion of a spine, positioning a second introducer in a second, different portion of the spine and, without removing the first and second introducers, introducing fluid into the first portion of the spine with the first introducer and introducing fluid into the second portion of the spine with the second introducer.

41 Claims, 11 Drawing Sheets

U.S. PATENT DOCUMENTS

| | | | |
|---|---|---|---|
| 4,551,133 A * | 11/1985 | Zegers de Beyl et al. | 604/66 |
| 4,583,974 A | 4/1986 | Kokernak | |
| 4,651,738 A | 3/1987 | Demer et al. | |
| 4,710,179 A | 12/1987 | Haber et al. | |
| 4,723,938 A | 2/1988 | Goodin et al. | |
| 4,740,203 A | 4/1988 | Hoskins et al. | |
| 4,758,223 A | 7/1988 | Rydell | |
| 4,810,249 A | 3/1989 | Haber et al. | |
| 4,832,692 A | 5/1989 | Box et al. | |
| 4,919,121 A | 4/1990 | Rydell et al. | |
| 4,940,459 A | 7/1990 | Noce | |
| 4,951,677 A | 8/1990 | Crowley et al. | |
| 5,004,472 A | 4/1991 | Wallace | |
| 5,009,662 A | 4/1991 | Wallace et al. | |
| 5,019,041 A | 5/1991 | Robinson et al. | |
| 5,021,046 A | 6/1991 | Wallace | |
| 5,047,015 A | 9/1991 | Foote et al. | |
| 5,084,060 A | 1/1992 | Freund et al. | |
| 5,137,514 A | 8/1992 | Ryan | |
| 5,147,300 A | 9/1992 | Robinson et al. | |
| 5,168,757 A | 12/1992 | Rabenau et al. | |
| 5,201,753 A | 4/1993 | Lampropoulos et al. | |
| 5,209,732 A | 5/1993 | Lampropoulos et al. | |
| 5,215,523 A | 6/1993 | Williams et al. | |
| 5,232,024 A | 8/1993 | Williams | |
| 5,273,537 A | 12/1993 | Haskvitz et al. | |
| 5,300,027 A | 4/1994 | Foote et al. | |
| 5,318,534 A | 6/1994 | Williams et al. | |
| 5,383,855 A | 1/1995 | Nicholson et al. | |
| 5,385,549 A | 1/1995 | Lampropoulos et al. | |
| 5,387,194 A | 2/1995 | Williams et al. | |
| 5,403,274 A | 4/1995 | Cannon | |
| 5,425,713 A | 6/1995 | Taylor et al. | |
| 5,429,606 A | 7/1995 | Robinson et al. | |
| 5,431,629 A | 7/1995 | Lampropoulos et al. | |
| 5,433,707 A | 7/1995 | Call | |
| 5,449,344 A | 9/1995 | Taylor et al. | |
| 5,449,345 A | 9/1995 | Taylor et al. | |
| 5,453,091 A | 9/1995 | Taylor et al. | |
| 5,458,571 A | 10/1995 | Lampropoulos et al. | |
| 5,459,700 A | 10/1995 | Jacobs | |
| 5,460,609 A | 10/1995 | O'Donnell | |
| 5,472,424 A | 12/1995 | Lampropoulos et al. | |
| 5,489,256 A | 2/1996 | Adair | |
| 5,533,514 A * | 7/1996 | Lavigne et al. | 600/557 |
| 5,545,133 A | 8/1996 | Burns et al. | |
| 5,562,614 A | 10/1996 | O'Donnell | |
| 5,599,301 A | 2/1997 | Jacobs et al. | |
| 5,625,144 A | 4/1997 | Chang | |
| 5,647,847 A | 7/1997 | Lafontaine et al. | |
| 5,653,739 A * | 8/1997 | Maurer et al. | 607/46 |
| 5,685,848 A | 11/1997 | Robinson et al. | |
| 5,692,500 A * | 12/1997 | Gaston-Johansson | 600/300 |
| 5,695,468 A | 12/1997 | Lafontaine et al. | |
| 5,704,913 A | 1/1998 | Abele et al. | |
| 5,728,064 A | 3/1998 | Burns et al. | |
| 5,741,229 A | 4/1998 | Robinson et al. | |
| 5,749,853 A | 5/1998 | O'Donnell et al. | |
| 5,752,935 A | 5/1998 | Robinson et al. | |
| 5,785,685 A | 7/1998 | Kugler et al. | |
| 5,808,203 A * | 9/1998 | Nolan et al. | 73/700 |
| 5,860,955 A | 1/1999 | Wright et al. | |
| 5,891,089 A | 4/1999 | Katz et al. | |
| 5,951,517 A | 9/1999 | Lampropoulos et al. | |
| 5,968,017 A | 10/1999 | Lampropoulos et al. | |
| 6,139,523 A | 10/2000 | Taylor et al. | |
| 6,159,161 A * | 12/2000 | Hodosh | 600/561 |
| 6,179,815 B1 | 1/2001 | Foote | |
| 6,190,354 B1 | 2/2001 | Sell et al. | |
| 6,224,561 B1 | 5/2001 | Swendson et al. | |
| 6,245,043 B1 | 6/2001 | Villette | |
| 6,258,042 B1 * | 7/2001 | Factor et al. | 600/557 |
| 6,368,314 B1 | 4/2002 | Kipfer et al. | |
| 6,370,420 B1 * | 4/2002 | Kraft | 600/431 |
| 6,387,054 B1 * | 5/2002 | Laserow | 600/552 |
| 6,394,977 B1 | 5/2002 | Taylor et al. | |
| 6,529,195 B1 * | 3/2003 | Eberlein | 345/441 |
| 6,533,757 B1 | 3/2003 | Lampropoulos et al. | |
| 6,544,228 B1 | 4/2003 | Heitmeier | |
| 6,676,664 B1 | 1/2004 | Al-Assir | |
| 6,856,315 B2 * | 2/2005 | Eberlein | 345/440 |
| 6,945,954 B2 * | 9/2005 | Hochman et al. | 604/67 |
| 2001/0039402 A1 * | 11/2001 | Prais et al. | 604/239 |
| 2002/0016567 A1 | 2/2002 | Hochman et al. | |
| 2002/0052562 A1 * | 5/2002 | Lipman | 600/557 |
| 2003/0028144 A1 * | 2/2003 | Duchon et al. | 604/151 |
| 2004/0260238 A1 | 12/2004 | Call | |
| 2005/0004518 A1 | 1/2005 | Call | |

* cited by examiner

SPINAL FLUID INTRODUCTION

RELATED APPLICATIONS

The present application claims priority to U.S. provisional application No. 60/448,529, filed Feb. 21, 2003, which application is incorporated herein by reference in its entirety.

TECHNICAL FIELD

The present invention relates to a system and method for introducing fluid into a spine.

BACKGROUND

Back pain is a common problem and is difficult to treat. Because of the complex anatomy and poor correlation of pathology and symptoms, diagnosis of the etiology of the pain may be difficult. Typical diagnostic procedures seek to determine whether a patient experiences back pain, leg pain, or a combination thereof. Back pain describes pain localized to the back, and often includes pain in the buttocks and upper thigh areas. This type of pain is understood to be caused by changes in one or more intervertebral discs and is termed discogenic back pain. The recognition that discs are potential pain sources has been a relatively recent discovery and is supported by anatomical studies that demonstrate nerve fibers within the disc, often increased by degenerative processes, and by direct stimulation of discs during discectomy procedures while the patient is under aware-state analgesia. Other causes of back pain have also been described including zygopophyseal (facet) joints, and other unknown causes.

In contrast, leg pain is often due to impingement of nerve roots as they exit the spinal canal. This causes pain to radiate into the areas the nerves innervate and creates a dermatomal pattern of pain related to the normal pattern of the nerve supply. This radicular pain is often due to herniation of intervertebral discs such that they bulge into the foramenal space, entrapping and pressing on the nerve. It is also believed to result from nucleus pulposus material extruding from the disc, resulting in noxious stimuli from degradation products such as phospholipase A2, and cytokines such as interleukins and TNFa.

Because the treatments for back pain and leg pain are often different, it is important to establish a proper diagnosis. Indeed, there is a strong correlation between patient selection and outcomes for spinal procedures, such that meticulous attention to diagnosis is essential. This is especially true as patients often exhibit a pattern of symptoms. Even sophisticated imaging capabilities do not always provide a clear diagnostic picture. Other diagnostic tools, such as physical examination and determination of patient history, are important.

A staple of physical examination is palpation of the painful region, to pinpoint where the pain is emanating from. This is difficult in the case of the intervertebral disc as it is anatomically located deep within the body and surrounded by bony structures. A procedure known as discography, discogram, disc stimulation, or more precisely as provocative discography, has been developed to overcome this limitation. Discography involves placing a needle into the intervertebral disc using fluoroscopic guidance and then injecting a fluid to create pressure to stimulate the disc, analogously to palpation. The injected fluid is typically a saline solution including radiopaque dye to allow for assessment of the disc morphology. A manually operated syringe is generally used to inject the fluid. The patient is maintained in an aware state such that they can provide feedback as to the pain induced by the injection, i.e. pressurization of the disc. Injection is performed one disc level at a time with the injectionist, e.g., a physician, switching connections prior to the start of the test at a specific level.

Pressure manometry has been used to monitor the pressure applied to the disc. This provides a more objective means for the injectionist to control pressure as compared to determining the pressure based upon the feel of a manually operated syringe. Studies have demonstrated a better diagnostic correlation when patients respond to low to moderate pressures (<50 psi) as compared to higher pressures (>50 psi).

Another aspect of performing a reliable discography diagnosis is how the injectionist interacts with the patient to obtain feedback on the pain stimulation. A patient's response to pain can include two components: the magnitude of pain and the quality of pain. The magnitude is often described as ranging from 0 to 10, where 0 is no pain, and 10 is the worst pain imaginable. The quality of pain is described as being concordant, meaning the back pain they are complaining of, or not concordant, pain different from their complaint, such as a general feeling of pressure. The ability to distinguish between concordant and non-concordant pain improves the determination of whether the disc being stimulated is the root cause of a patient's back pain, or is evoking pain unrelated to their symptoms. A low pressure, concordant pain response at 1 or 2 spine levels, e.g., spinal discs, accompanied by no pain at a level above or below (control level) the painful discs is generally understood to provide the most definitive diagnosis for discogenic pain.

Patient responses from a discography procedure are recorded by the injectionist or assistant using one or more forms. Other parameters, such as the volume of fluid injected are added to the patient responses. A separate chart can be used to determine the peak pressure in the disc as well as any leakage.

SUMMARY

One aspect of the present invention relates to a fluid introduction system. In one embodiment, the fluid introduction system includes wan introducer configured to create a pressure of at least 10 psi (69 kPa) within a spine, and an operator configured to actuate the introducer to introduce fluid into the spine according to a predetermined fluid introduction profile.

Embodiments of this aspect of the invention may include one or more of the following features:

The introducer can be configured to create a pressure of at least 10 psi (69 kPa) in an intervertebral disc.

The predetermined fluid introduction profile can be the introduction of fluid at a constant rate. The introducer can be configured to introduce a repeatable amount of fluid into the spine. The introducer can be configured to introduce fluid into the spine at a repeatable rate. The introducer can be configured to introduce a non-pulsatile flow of fluid into the spine. The introducer can be configured to create a pressure of at least 20 psi (138 kPa) in an intervertebral disc.

According to another aspect of the invention, a fluid introduction system comprises an introducer configured to introduce fluid into a spine of a patient, an operator configured to actuate the introducer to introduce fluid into the spine of the patient, a computer readable medium having code for receiving fluid introduction data indicative of a fluid introduction parameter, and for receiving response data indicative of a response of the patient at a time related to a time of the fluid introduction data.

Embodiments of this aspect of the invention may include one or more of the following features:

The fluid introduction parameter can be a pressure within an intervertebral disc of the patient at the time of the fluid introduction data and/or a total amount of fluid introduced into an intervertebral disc of the patient at the time of the fluid introduction data.

The fluid introduction parameter can be configured to obtain the response data from an observation of the patient and/or to obtain the response data upon a response by the patient.

The fluid introducer can be configured to create a pressure of at least 100 kPa within the spine.

According to another aspect of the invention, a fluid introduction system includes an introducer configured to introduce a non-pulsatile flow of fluid into a spine, and an operator configured to actuate the introducer. The introducer has a flow rate-dependent impedance opposing the introduction of the fluid. The operator includes code to control the actuation of the introducer based at least in part upon impedance data indicative of the impedance.

Embodiments of this aspect of the invention may include one or more of the following features:

The introducer can include an identifier including the impedance data and the operator can be configured to receive the impedance data from the identifier of the introducer. The operator can include code to determine the impedance data based upon an actuation of the introducer.

The fluid introduction system can include a pressure sensor configured to provide pressure data indicative of a pressure of fluid present in the introducer, a fluid introduction sensor configured to provide fluid introduction data indicative of at least one of (a) a rate of fluid introduction and (b) an amount of fluid dispensed from the introducer, and the operator can include code to determine the impedance data based upon the pressure data and the fluid introduction data.

According to another aspect of the invention, a fluid introduction system includes a first introducer configured to introduce fluid into a first portion of a spine, a second introducer configured to introduce fluid into a second, different portion of a spine, and an operator configurable to concurrently actuate the introduction of fluid into the first portion of the spine by the first introducer and the introduction of fluid into the second portion of the spine by the second introducer.

Embodiments of this aspect of the invention may include one or more of the following features:

The first and second introducers can be respectively configured to introduce fluid into first and second different intervertebral discs, such as to provide a simultaneous pressure of at least 10 psi (69 kPa) in each of the first and second intervertebral discs. The first and second introducers can be actuable independently of one another.

According to another aspect of the invention, a fluid introduction system includes an introducer configured to introduce a fluid having a dynamic viscosity of at least 750 Pa into a spine and an operator configured to actuate the introducer according to a predetermined introduction profile.

Embodiments of this aspect of the invention may include one or more of the following features:

The fluid can be at least one of a polymeric fluid and a non-Newtonian fluid.

The introducer can have an impedance that opposes the actuation of the introducer, the impedance is, e.g., dependent upon the viscosity of the fluid and the fluid introduction system can be configured to obtain impedance data indicative of the dynamic viscosity of the fluid.

According to another aspect of the invention, a syringe includes a reservoir, a plunger slidable with respect to the reservoir to apply pressure to fluid therein, and a pressure transducer secured with respect to the plunger and configured to be in direct contact with fluid in the reservoir.

Embodiments of this aspect of the invention may include one or more of the following features:

A receivable portion of the plunger can be receivable within the reservoir. The syringe can include a cap secured with respect to the receivable portion of the plunger. The pressure transducer can be disposed between at least a portion of the cap and at least a portion of the receivable portion of the plunger.

The cap can include a hole configured to allow fluid present within the reservoir to contact the pressure transducer.

The cap and the plunger can be configured so as not to be rotatable with respect to one another when the cap is secured with respect to the receivable portion of the plunger.

The cap and the receivable portion of the plunger can each comprise an asymmetrical portion. The asymmetrical portions of the cap and plunger can mate with one another to secure the cap with respect to the plunger.

According to another aspect of the invention, a fluid introduction system includes an introducer configured to introduce a fluid into a spine, and an operator configured to actuate the introducer to introduce fluid into the spine according to a predetermined fluid introduction profile.

According to another aspect of the invention, a method for introducing fluid includes positioning a first introducer in a first portion of a spine, positioning a second introducer in a second, different portion of the spine and, without removing the first and second introducers, introducing fluid into the first portion of the spine with the first introducer and introducing fluid into the second portion of the spine with the second introducer.

Embodiments of this aspect of the invention may include one or more of the following features:

The first and second portions of the spine can be different intervertebral discs.

Introducing fluid into the first portion of the spine can include creating a pressure of at least 10 psi (69 kPa) in the first portion of the spine, and introducing fluid into the second portion of the spine can include creating a pressure of at least 10 psi (69 kPa) in the second portion of the spine. Introducing fluid into the first portion of the spine can at least partially overlap the step of introducing fluid into the second portion of the spine.

Advantages of the invention may include one or more of the following:

Positioning at least two introducers is advantageous over removing and reinserting a needle because such movement can cause the patient to anticipate pain. Additionally, the present system and method reduces the risk of infection because a syringe need be connected and removed only once during the procedure. Use of multiple introducers decreases the time required to perform a discography diagnostic by reducing the need for switching the injection system between needles, and increases the degree of flexibility for testing and retesting various levels.

A method and system have been developed that improves the overall quality of introduction of fluid into the spine, e.g., during discography, vertebroplasty, and/or nucleus augmentation. With respect to discography, the improvement includes the ability to perform the test in a more reproducible manner, improving clinical efficacy.

The current system has design features that allow for a more standardized procedure with regards to patient interaction and feedback on pain responses. This is achieved by having a standardized dialog for the injectionist and patient such that the injectionist does not provide inadvertent cues to the patient that could influence the patient's response, and that instructs the patient concerning their role in the procedure. Properly "blinding" the patient as to when injections are performed is an example of how to avoid responses that could negatively influence the value of the procedure. There is a substantial psychological component of pain, and this appears to be exacerbated in chronic pain sufferers such as many people with back pain. A patient interface module of the system is also an embodiment. This includes a touch panel screen where the patient traces pain as to intensity and quality (concordant or not). Another embodiment is a squeeze bulb for intensity of pain.

Another aspect of performing a standardized provocative disc diagnosis involves management of the data such that a diagnostic report can be generated.

The system of the current invention has a central data logger that correlates pressure, flow and volume readings from a syringe manometry device with the injection sequence and patient response data. This central processor further performs a diagnostic algorithm such as described by the ISIS (International Spine Injection Society) Guidelines (modified to incorporate the more robust data provided with this enhanced system), such that a diagnostic report is generated. The central processor has user interfaces such as a key board that allows for entry of patient name, age, sex, date, and other key demographic and procedure information such that reporting, billing and other functions are expeditiously performed.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
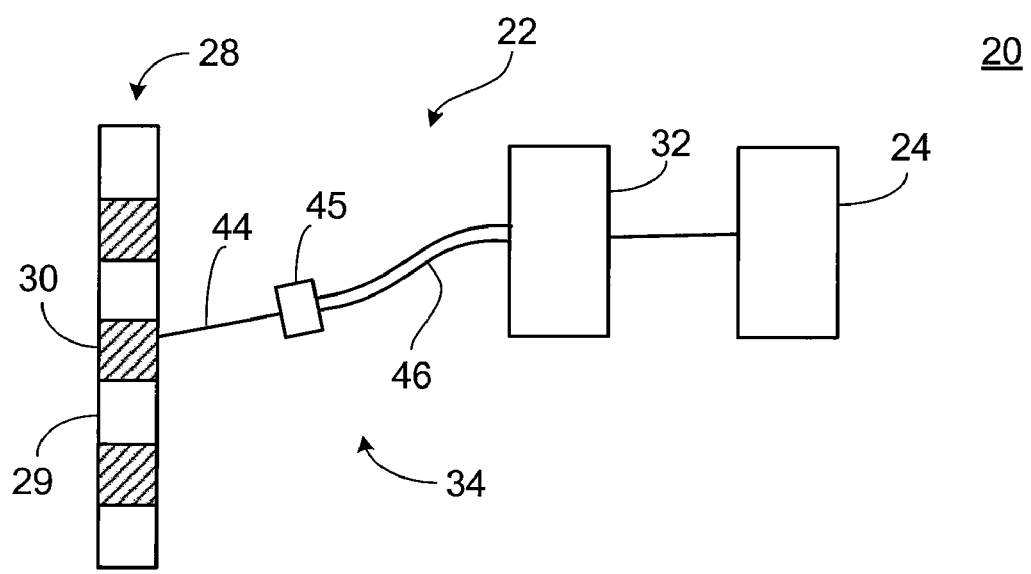
FIG. 1 is a schematic illustration of a fluid introduction system.

Referring to FIG. 1, a fluid introduction system 20 includes an introducer 22 and an operator 24. Introducer 22 introduces fluid into a spine 28, such as into a vertebral body 29 or an intervertebral disc 30 thereof. Operator 24 actuates the introduction of fluid by introducer 22, preferably according to a fluid introduction profile.

Figure 2:
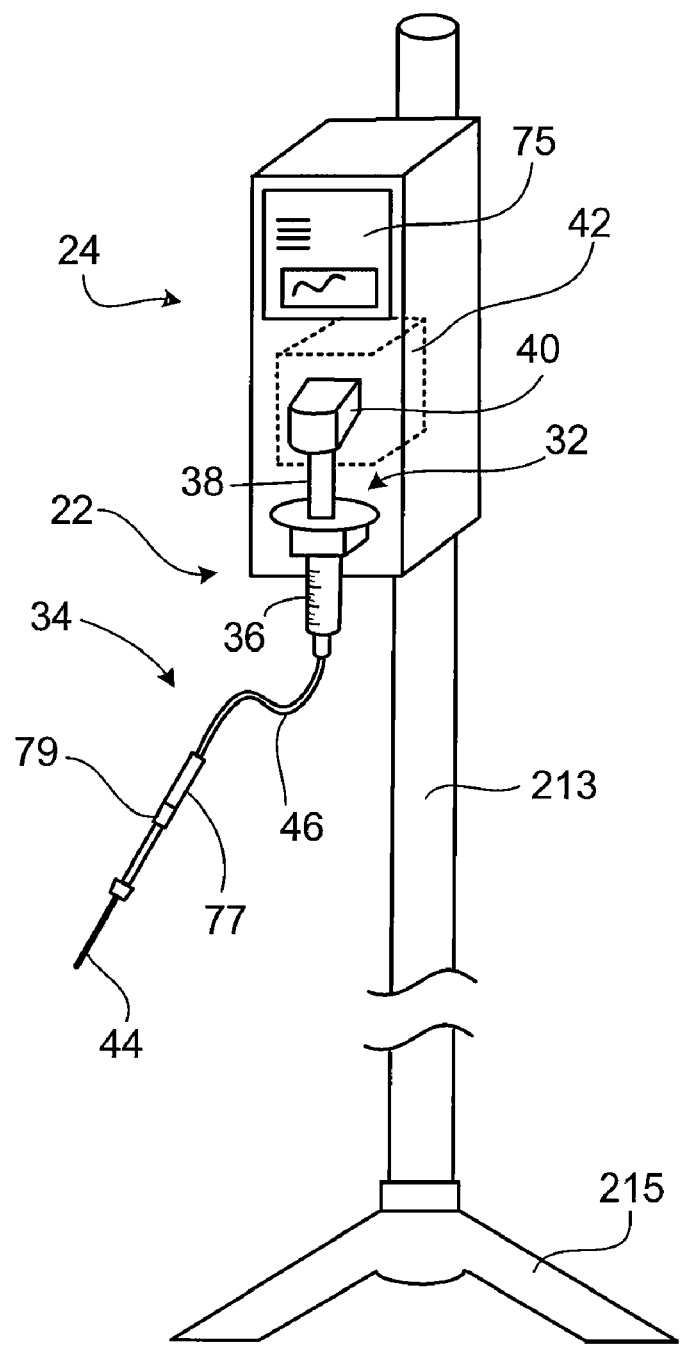
FIG. 2 is an illustration of the fluid introduction system of FIG. 1.

Referring also to FIG. 2, introducer 22 includes a fluid drive assembly 32 and a fluid introduction assembly 34. Fluid drive assembly 32 includes a fluid reservoir, e.g., a 30 ml syringe 36, a pressure applicator, e.g., a plunger 38 slidably received within syringe 36, for applying pressure to fluid therein, an actuator arm 40 for moving plunger 38, and a motor 42 for driving actuator arm 40. Fluid introduction assembly 34 includes a fluid introduction member, e.g., a needle 44 for positioning in spine 28, and tubing 46 interconnecting syringe 36 and needle 44 via a connector 45. Syringe 36 connects to tubing 46 via a fitting, e.g., a Luer lock fitting, or syringe 36 and tubing 46 can be otherwise mechanically or adhesively secured. Tubing 46 has a length of about 1.75 meters. Introduction assembly 34 includes a pressure transducer 77 for providing pressure data indicative of a pressure within assembly 34 and a remote control 79 to receive an event marker input from a user and allow the user to control system 20 such as by initiating, stopping, or pausing the introduction of fluid and setting fluid introduction parameters. Remote control 79 can be in hardwired or wireless communication with operator 24 and can be integral with system 20 or mechanically free thereof. Introducer 22 and operator 24 are securely supported by a support 213 and a base 215.

Figure 3:
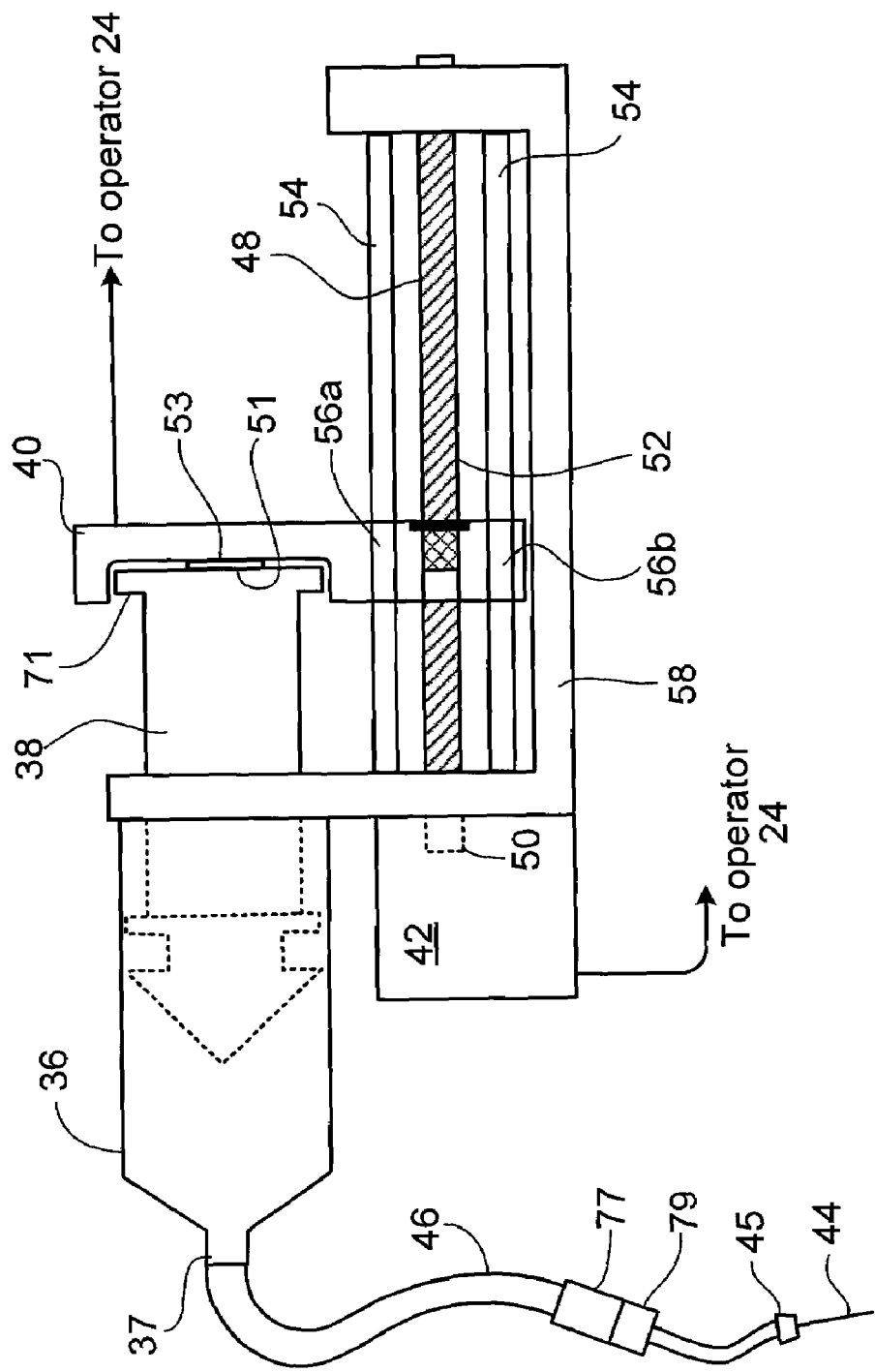
FIG. 3 is an illustration of the fluid drive assembly of the fluid introduction system of FIG. 1.

Referring to FIG. 3, motor 42 is, e.g., an electric motor, such as the Haydon Switch and Instruments size 17 no. E43H4A-05 stepper motor (Waterbury, Conn.). Fluid drive assembly 32 includes a drive screw 48 secured to an output shaft 50 of motor 42, and rotatably coupled to a drive nut 52. Drive screw 48 is supported by a fluid drive bracket 58 and two support shafts 54 coupled to drive screw 48 by bearings 56a, 56b. Bearings 56a, 56b are coupled to drive nut 52 to move linearly with drive nut 52. Axial movement of drive nut 52 is transferred to actuator arm 40 by bearings 56a, 56b. Support shafts 54 distribute the load applied to drive screw 48. Motor 42 is reversible such that the fluid can be introduced and extracted from the spine using system 20.

Figure 4:
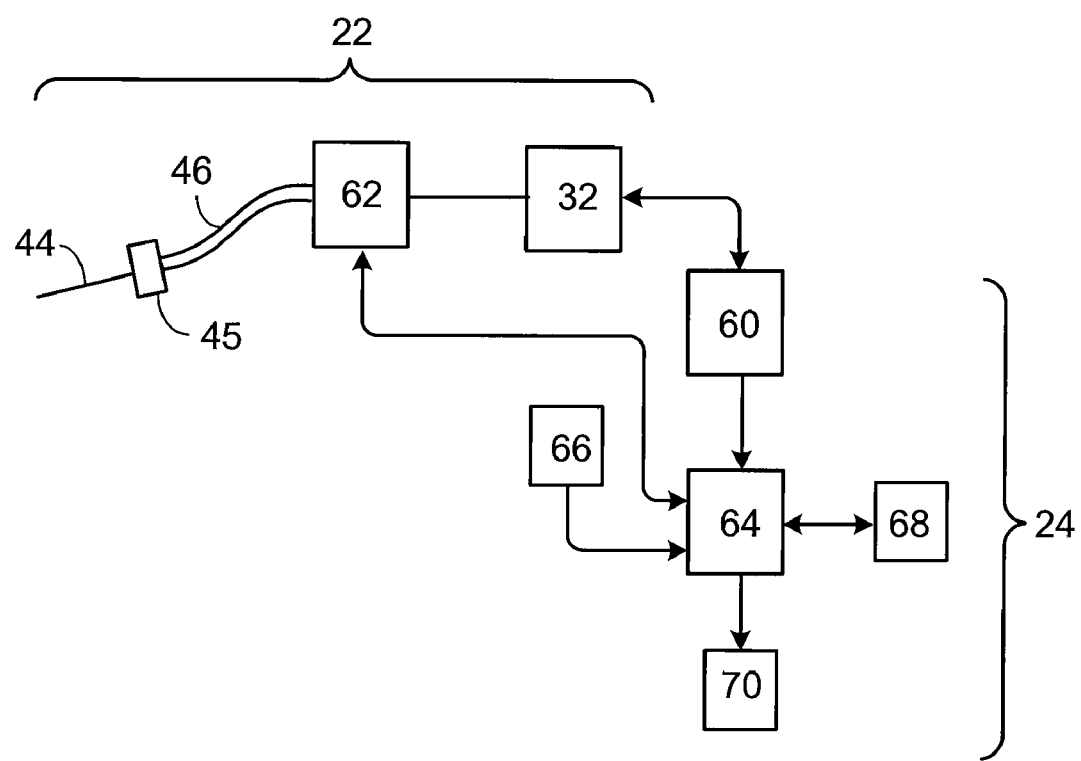
FIG. 4 is an illustration of sub-systems of the fluid introduction system of FIG. 1.

Referring to FIG. 4, fluid introduction system 20 includes a number of sub-systems, e.g, fluid drive assembly 32 of introducer 22, and operator control subsystem 60, pressure monitoring 62, data acquisition 64, patient feedback 66, user interface 68, and test report 70 of operator 24. These subsystems and other aspects of the present invention are discussed below.

Introducer

Referring again to FIGS. 1 and 2, introducer 22 introduces fluid to a spine, such as into a disc or vertebral body thereof. Introducer 22 minimizes variations from test to test in the amount of fluid introduced and/or the pressure created within the spine, which can occur due to tubing variables or volume changes and allows for corrections due to pressure losses at, for example, connector 45. System components exhibit minimal volume change upon pressurization to about 100 psi (690 kPa), to about 150 psi (1035 kPa), e.g., to about 200 psi (1380 kPa). System 20 is preferably configured to generate a pressure in a spine of at least about 10 psi (69 kPa), 20 psi (138 kPa), 50 psi (245 kPa), 100 psi (690 kPa), 150 psi (1035 kPa), e.g., at least about 200 psi (1380 kPa). Thus, operator 22 can use movements of the motor 42 to determine volume data indicative of the volume of fluid introduced into the spine, preferably to within 0.1 ml. A given volume of fluid can be repeatedly introduced with a standard deviation of about 0.2 ml or less, such as about 0.1 ml or less. Introducer 22 dispenses the fluid at a minimum rate of 0.05 ml s$^{-1}$. For example, introducer 22 can introduce a total volume of at least about 20 ml of fluid at from 0.1 ml s$^{-1}$ to 1 ml s$^{-1}$, such as in 0.1 ml s$^{-1}$ increments. Introducer 22 is preferably configured to introduce a non-pulsatile flow of fluid, e.g., a given volume of fluid, e.g., at least 0.3 ml or at least 0.5 ml, can be introduced at a pressure of at least 15 psi with the volume of fluid being introduced with a relative variation in flow rate of less than 10%, e.g., less than 5%.

Introducer 22 can introduce any of various fluids including but not limited to Newtonian fluids, non-Newtonian fluids, and polymeric fluids into a spine. For example, the fluid can be a typical discography fluid, such as a saline solution optionally including a radio-opaque contrast agent. Alternative fluids include a hardenable medium, such as bone cement, and a hydrogel, such as used in nucleus augmentation or replacement. An exemplary bone cement includes a polymer, e.g., polymethylmethacrylate, a contrast agent, e.g., sterile barium powder, and an antibiotic. The hardenable medium can have a dynamic viscosity of at least 250 Pa, 500 Pa, 750 Pa, 1000 Pa, such as at least about 1200 Pa.

Pressure Monitoring Subsystem

Pressure monitoring subsystem 62 determines the pressure of fluid present within introducer 22 and provides pressure data for use by the operator control subsystem 60 in feedback control loops. Pressure monitoring subsystem 62 includes at least one pressure transducer and is discussed in more detail with respect to operator control subsystem 60 and syringe 36. The pressure transducer is located within introducer 22, such as in fluid introduction assembly 34 or fluid drive assembly 32, preferably in direct contact with fluid present within introducer 22. Pressure data can include, for example, pressure versus time data, a cracking pressure (the pressure at which internal pressure within the disc is overcome and fluid begins being introduced) of an intervertebral disc, and a maximum pressure created. Each of these pressure data preferably include a time component indicative of a time at which the particular pressure occurred.

System 20 is preferably configured to determine the cracking pressure of a spinal disc. For example, the cracking pressure can be determined by monitoring the pressure of fluid within introducer 22 as pressure is applied to syringe 36. When the cracking pressure is reached, a pressure variation, such as a pressure drop, occurs. System 20 can mark the cracking pressure and time the cracking pressure was reached as an event that can be reported using report sub-system 70 discussed below.

Operator Control Subsystem

Operator control sub-system 60 improves the repeatability and accuracy at which the fluid is introduced into the spine and allows for various fluid introduction modes. System 20 can be used in a manual mode or a preprogrammed mode. In the manual mode, the user controls the starting and stopping of system 20 as well as any pauses in fluid introduction. A user interface 68 including a graphical interface 75 of operator 24 accepts user inputs of control parameters, test conditions, e.g., the disc or disc to be tested, and provides the user with real time data indicative of at least one of fluid pressure (pressure data), an amount (e.g., volume) of fluid introduced (volume data), and a rate of fluid introduction (rate data). Pressure data indicative of the pressure of fluid within introducer 22 is obtained from a pressure transducer, as discussed below. Volume data indicative of the amount of fluid introduced is obtained from the actuation of syringe 36 by motor 42. Rate data indicative of the rate of fluid introduction is determined from the volume data as a function of time. Each of the volume and rate data preferably includes a time component indicative of a time associated with the particular data.

Graphical interface 75 displays data indicative of system 20 parameters, e.g., fluid introduction parameters related to the introduction of fluid, during a test. For example, real time pressure data, volume data, and rate data can be displayed graphically, numerically, or through combination thereof. The location of the disc or disc into which fluid is being introduced can be displayed. Event markers and patient response data can also be displayed, preferably by showing the temporal relationship between the system 20 parameters and the event marker or patient response.

In the preprogrammed mode, fluid is introduced according to a predetermined fluid introduction profile under microprocessor control, e.g, using computer code residing in a computer readable medium. During the introduction of fluid according to a predetermined fluid introduction profile, control subsystem 60 controls the introduction of fluid to achieve a given fluid pressure, a given pressure profile, introduce a given volume of fluid, or introduce fluid at a given rate or rate profile as specified by the user or manufacturer. Fluid introduction profiles calling for variable introduction according to these parameters can be used. System 20 includes control loops, as discussed below, which can dynamically modify the introduction of fluid during the introduction according to a predetermined fluid introduction profile.

System 20 can be configured to switch between the control of fluid introduction according to a given combination of parameters, e.g., one or more of pressure, volume, and rate, and control of fluid introduction according different combination of such parameters. For example, system 20 can allow introduction of fluid according to one combination of parameters until the cracking pressure of a disc is reached and then switch the introduction of fluid according to a different combination of parameters thereafter. The switch can be initiated by system 20 or a user thereof.

The control sub-system 60 incorporates pressure, volume, and/or rate feedback control loops, e.g., proportional-integral-derivative (PID) control loops, to control the fluid introduction based upon pressure data, volume data, or rate data, respectively. Of course, a feedback control loop can utilize a combination of these and other parameters to control the fluid introduction. For example, during fluid introduction, increased resistance to the fluid introduction can cause a pressure increase. Control sub-system 60 includes a feedback loop configured to reduce a rate of advance of actuator arm 40 until the measured pressure returns to a value within a predetermined range. Control sub-system 60 can also include a feedback loop that notifies a user of a pressure decrease, which can be indicative of a pressure loss or leak. The user maintains a manual override during preprogrammed fluid introduction. All control loops discussed herein can be implemented as computer code residing in a computer readable medium.

As discussed above, a pressure variation can occur when the cracking pressure of a disc is reached during a test. Control sub-system 60 can include a control loop to minimize fluctuations in the rate of fluid introduction that might otherwise result from the pressure variation. For example, if a drop in pressure occurs, the control loop can reduce the actuation rate of motor 42 to compensate for the pressure drop in pressure. Thus, system 20 can maintain the introduction of fluid at a constant rate.

Operator control sub-system 60 can correct the pressure data for differences between the pressure created within a spine by the introduction of fluid and the pressure of the fluid within introducer 22. A variable that can cause such differences is the resistance to fluid introduction caused by the impedance of the syringe 36 and fluid introduction assembly 34. For example, tubing with a narrower bore and/or longer length will have a higher impedance than tubing with a wider bore and/or shorter length. Also, a needle with a narrower bore and/or longer length will have a higher impedance than a needle with a wider bore and/or shorter length. During the introduction of fluid, the impedance can cause the pressure data from the introducer to be higher than the actual pressure created in the spine. Operator control subsystem 60 includes control loops that correct the pressure data based upon impedance data indicative of the impedance to fluid introduction of fluid introduction assembly 34 and syringe 36. Exemplary impedance data are indicative of the resistance to fluid flow of the syringe and fluid introduction assembly and can include, e.g, at least one of the gauge of the needle, the length of the needle 44, the inner diameter of the tubing, and the length of tubing 46.

The impedance data can be determined on the basis of the properties of the syringe and fluid introduction assembly 34, empirically, or by a combination thereof. For example, as discussed below, introducer 22, e.g., syringe 36, can include the impedance data. Empirical determination of the impedance data can be performed as follows. Operator control subsystem 60 actuates fluid drive assembly 32 by an amount sufficient to dispense a given amount of fluid. The actuation is preferably performed prior to inserting needle 44 into a spine. Pressure data are obtained during the actuation. The impedance data are determined based upon the pressure during actuation and the volume of fluid dispensed. Operator control subsystem 60 allows fluid variables including viscosity to be input for use in empirical impedance determination.

As discussed above, system 20 can be used to introduce hardenable media, e.g., bone cements, into a spine, such as in vertebroplasty. The viscosity of a hardenable medium increases as it cures and the medium is preferably not introduced into the spine until having reached a predetermined viscosity. Operator control subsystem 60 includes a viscosity determination control loop to determine when the hardenable medium has reached the predetermined viscosity suitable for introduction. Prior to introducing the hardenable medium into the spine, the viscosity determination control loop actuates the fluid drive subsystem to dispense a given amount of the hardenable medium and pressure data are obtained during the dispensation. The resistance of the fluid to the dispensation appears as an increase in pressure within the introducer 22 and is a function of the viscosity of the hardenable medium. The viscosity of the hardenable fluid is determined using the pressure data and calibration data for the particular hardenable fluid. Impedance data, as described above, may also be used in the determination of the viscosity.

Figure 5:
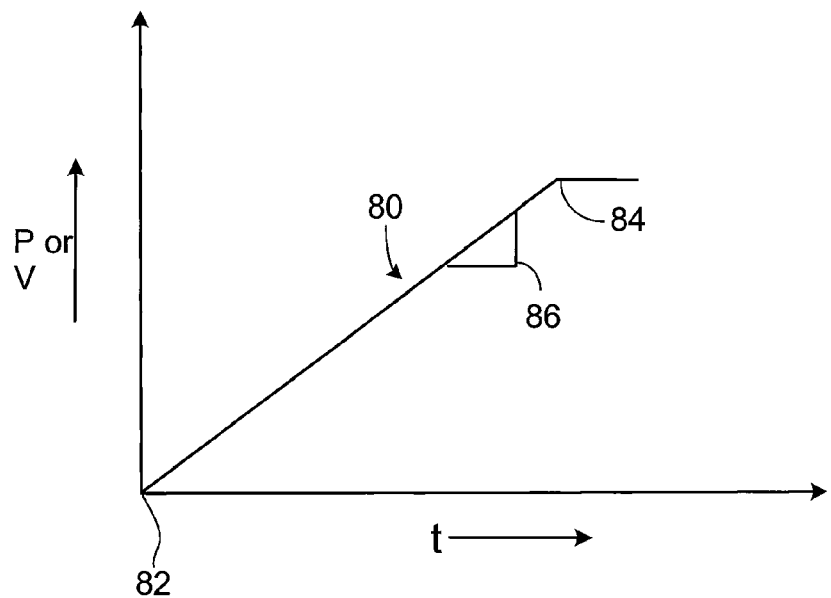
FIGS. 5 and 6 are illustrations of flow rate graphs.
Figure 6:
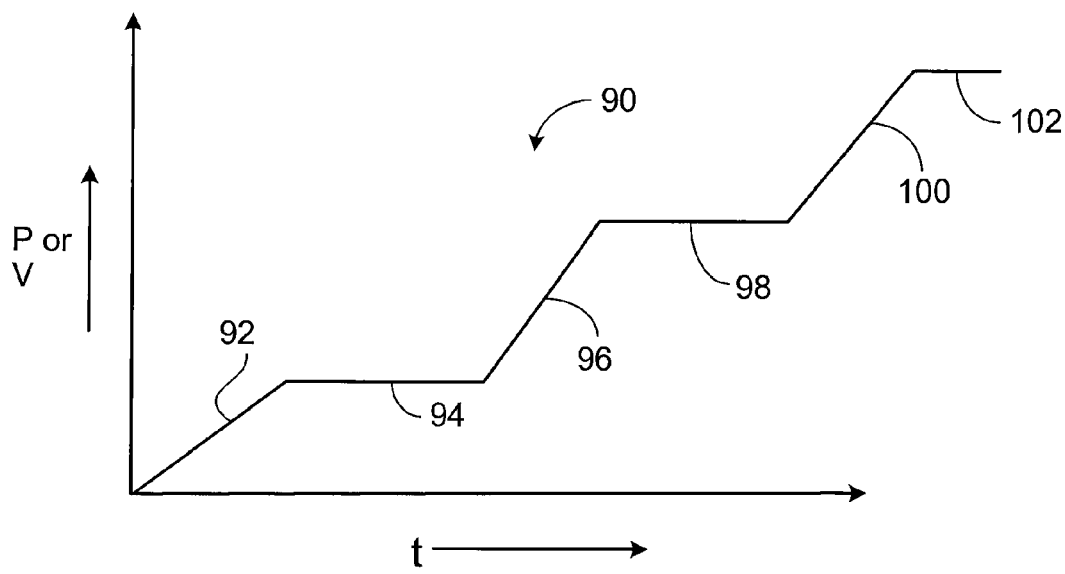

Referring to FIGS. 5 and 6, fluid can be introduced according to a number of different predetermined fluid introduction profiles. During a continuous fluid introduction profile 80, a pressure within the spine and/or an amount of fluid introduced into the spine increase continuously between a starting point 82 and an end point 84. A slope 86 of profile 80 can be varied. During preferred continuous fluid introduction profiles, a rate of fluid introduction is constant, such as between starting point 82 and end point 84. Thus, a pressure within the disc and the total volume of fluid introduced increase linearly. Non-linear fluid introduction profiles during which the rate of fluid introduction varies can also be used.

As seen in FIG. 6, during a ramp fluid introduction profile 90, pressure increases 92 within the spine to a first level 94 and is then held at this level for a time and then pressure increases 96 to a second level 98 and is then held for a period of time. First and second pressure levels and the duration of time for which these levels are held can be arbitrary or predetermined. One or more additional pressure increases 100 and holds 102 can be added until a desired upper pressure or volume limit is reached. The increases in pressure can be at a constant or variable rate as described above.

Syringe

Figure 7:
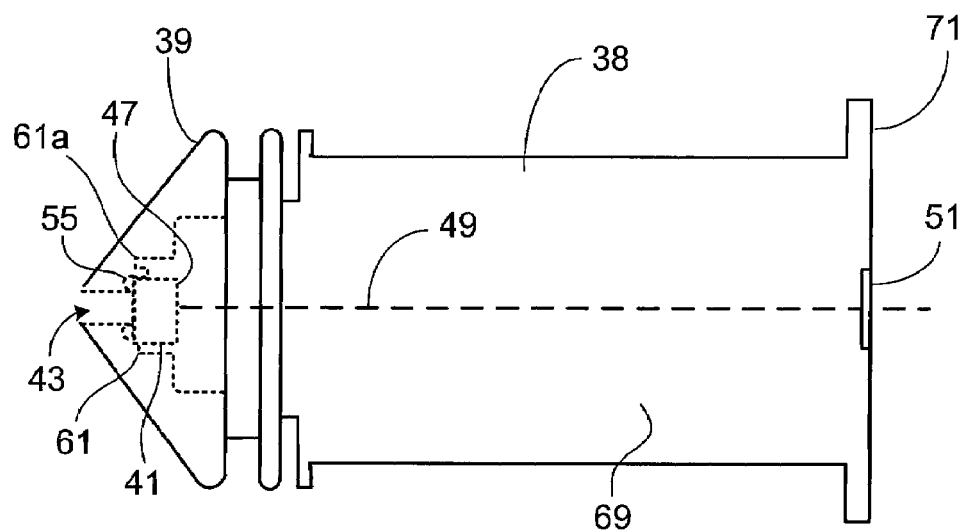
FIG. 7 is a side-view of a plunger and cap with pressure transducer.
Figure 8:
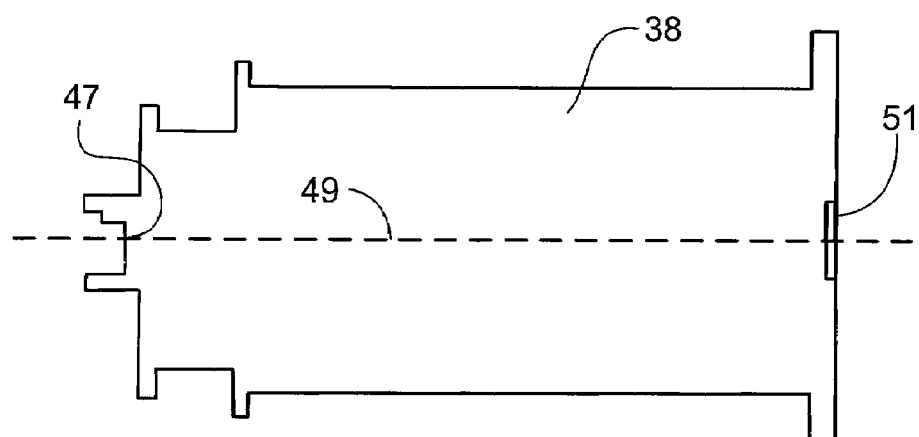
FIG. 8 is an illustration of the plunger of FIG. 7 with the cap and pressure transducer removed.

Returning to FIG. 2, syringe 36 provides a reservoir for fluid to be introduced into the spine and is preferably clear to allow a user to determine the fluid level therein and ascertain the presence of bubbles. Plunger 38 slides with respect to syringe 36 to pressurize fluid therein causing fluid introduction assembly 34 to dispense fluid. Referring also to FIGS. 7 and 8, plunger 38 includes a cap 39. Cap 39 is formed of a resilient material, e.g., a silicone-based material, to provide a seal sufficient to withstand pressures without substantial leakage of up to 150 psi within syringe 36.

Cap 39 includes a pressure transducer 41, e.g., a piesoresistive pressure sensor, such as an ICSensors Model 1471 pressure transducer, and a passage 43 configured to place a pressure sensing portion 101 of transducer 41 in direct contact with fluid present within syringe 36. Pressure transducer 41 provides pressure data indicative of a pressure of the fluid. Plunger 38 includes first contacts 47, a conductor 49 extending along a shaft 69 of plunger 38, and second contacts 51 for communicating pressure data away from cap pressure transducer 41. Actuator arm 40 includes contacts 53 that mate with contacts 51 (FIG. 3) such that the pressure data are received by operator 24, which is in communication with fluid delivery device 32. Transducer 41 preferably provides pressure data accurate to within 2% of the actual pressure over a range of 0-100 psig (0-690 kPa), e.g., 0-150 psig (0-1035 kPa). A secondary pressure transducer can be used to act as a backup to transducer 41.

Cap 39 and plunger 38 securely seat pressure transducer 41 to limit leaks and loss of electrical connectivity during use. Cap 39 includes a gasket seal 55 surrounding passage 43 and an inner wall 57 providing a secondary seal around the sides of the pressure transducer to limit fluid coming in contact with the electrical contacts of pressure transducer 41 and plunger 38. Adhesive may be used to further secure pressure transducer 41 with respect to cap 39 and to limit loss of electrical contact. First contacts 47 are preferably molded as part of plunger 38 to provide a solder-less contact that reduces leakage and improves electrical isolation.

Figure 9:
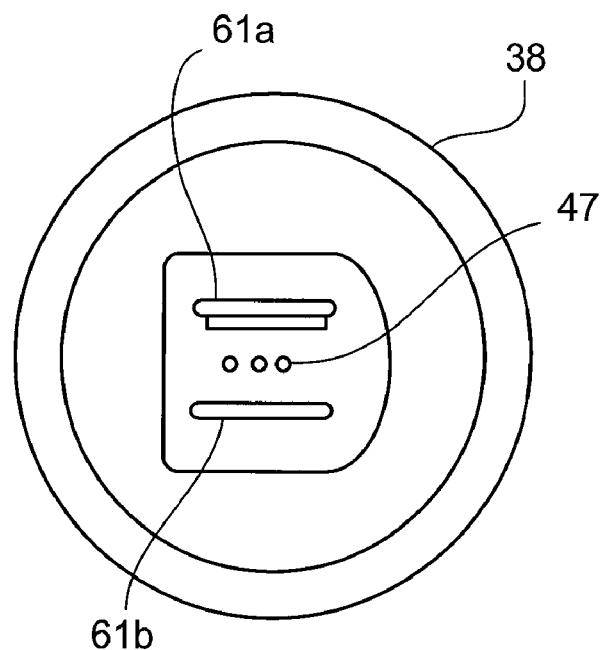
FIG. 9 is a front view of the plunger of FIG. 8.
Figure 10:
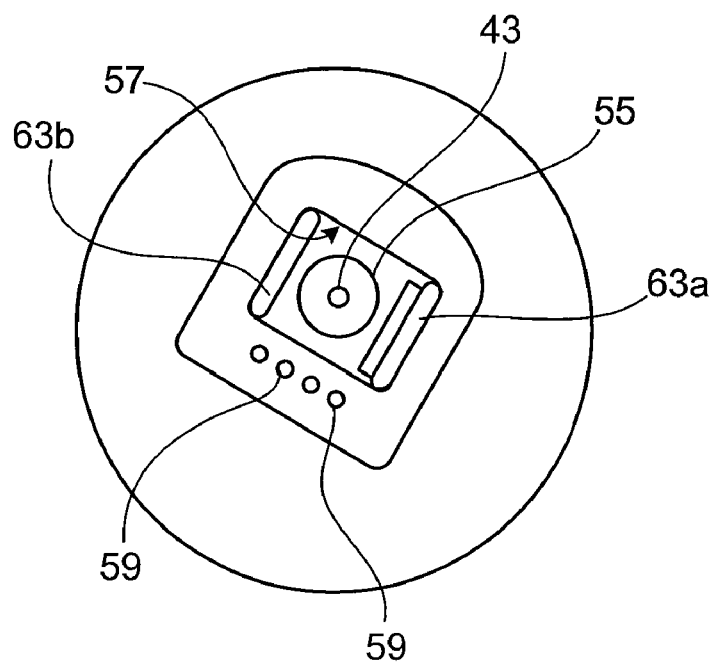
FIG. 10 is a rear view of the cap of FIG. 7 with the plunger and pressure transducer removed.

Referring to FIGS. 9 and 10, plunger 38 includes projections 61a, 61b and cap 39 includes notches 63a, 63b for receiving projections 61a, 61b when the plunger and cap are mated. Additionally, cooperation between projections 61a, 61b and notches 63a, 63b secures pressure transducer 41 on at least two sides to limit lateral motion with respect to cap 39 and plunger 38. Projections 61a, 61b and notches 63a, 63b are preferably asymmetric so that cap 39 can be secured to plunger 38 in only one orientation. Cap 39 includes locating marks, e.g., locating pins 59 so that pressure transducer 41 can be secured with respect to cap 39 in only one orientation. The asymmetric projections, notches and the locating marks facilitate proper assembly of cap 39, plunger 38, and transducer 41. The asymmetrical portions of the cap and plunger can mate with one another to secure the cap with respect to the plunger. Cap 39 and plunger 38 are preferably not rotatable with respect to one another when the cap is secured with respect to the plunger.

Plunger 38 includes a butt 71 that can also be asymmetric so that plunger 38 can be positioned in only one orientation with respect to fluid delivery device 32 thereby assuring proper communication between contacts 51 of plunger 38 and contacts 53 of actuating arm 40 (FIG. 3). Because contacts 51 of plunger 38 and contacts 53 of actuator arm 40 are brought into electrical communication by positioning syringe 36, no additional electrical contacts need be made by a user. Fluid delivery device 32 determines when contacts 53 of actuator arm 40 contact contacts 51 of butt 71 of plunger 38 such that additional movement of actuator arm 40 would pressurize syringe 36 and/or dispense liquid. Fluid drive subsystem 32 can also include a sensor (not shown) to determine when actuator arm 40 has been fully extended.

As discussed above, syringe 36 and plunger 38 can include impedance data indicative of an impedance to fluid introduction of syringe 36 and fluid introduction assembly 34. In a preferred embodiment for a particular fluid drive assembly 32 and fluid introduction assembly 34 provided by the manufacturer, impedance data are readout at contacts 51 of plunger 38 by contacts 53 of actuator arm 40 (FIG. 4). For example, a particular arrangement of contacts 51 can be indicative of the impedance data. Thus, when a syringe, plunger, and fluid introduction assembly are positioned for use in fluid delivery system 32, the impedance data are read at contacts 53 and received by operator 24. The operator control subsystem 60 includes control loops that control the introduction of fluid based at least in part upon the impedance data. In one embodiment, the fluid introduction assembly 34 is a disposable assembly to be discarded after a single use. In such an embodiment, operator 24 is preferably configured to recognize each assembly and limit the assembly to a single patient use.

Fluid introduction assembly 34, can include other data indicative of properties of the system, e.g., an expiration date of the assembly and/or properties of fluid within the assembly, e.g., composition and viscosity, if preloaded by the manufacture. These data and the impedance data may be encoded using, e.g., radio frequency identification, bar coding, and or an arrangement of contacts 51, as discussed above. Operator 24 can be configured, such as through computer code, to read the data, e.g., expiration date data, and prevent use of an expired fluid introduction assembly. Operator 24 can be configured, such as through computer code, to read data indicative of properties of preloaded fluid and adjust fluid introduction profiles according to the properties of the preloaded fluid.

Data Acquisition

Data acquisition sub-system 64 increases the efficiency of system 20 by collecting substantially all patient-related data in one location such that the patient-related data can be readily incorporated into a final report. Data acquisition subsystem 64 also allows for accurate and real time data acquisition and monitoring facilitating the diagnostic capability of fluid introduction procedures such as discography. These and other features of data acquisition sub-system 64 can be implemented by a computer readable medium including computer code.

Data acquisition subsystem 64 records user inputs, such as a patient identifier, the location(s) of the spine receiving injected fluid, the number of locations receiving fluid, and the order of fluid introduction into these locations. Other data, such as the cracking pressure of the disc, maximum pressure reached in each disc, the presence of pressure leakage, equilibrium pressure in each disc, and volume of fluid introduced can also be recorded. These data can be recorded in any one of a number of digital media including flash cards, floppy discs, CD etc. The data acquisition subsystem also receives event marker inputs, such as from remote control 79. The event marker inputs may be indicative of a patient response observed by the user or other condition to be noted.

Patient Feedback Sub-System

Patient feedback sub-system 66 receives real-time quantifiable response data of the patient. The response data preferably includes a patient's pain level and concordance and can include data input directly by the patient using, e.g. a squeeze ball or a sliding device correlated to a visual analog scale (VAS) from 0-10 and including an axis for relating level of concordance/non-concordance of the pain, and/or observed data such as physiological parameters including electromyographic response data. Other observed data include audiovisual recordings of facial responses such as wincing, grimacing, clenching of the jaw and the like.

The response data is communicated to data acquisition sub-system and temporally correlated with actual measurements of disc pressure and the volume of fluid introduced into one or more discs. These and other features of patient feedback sub-system 66 can be implemented by a computer readable medium including computer code.

Report Sub-System

Report sub-system 70 provides a final report that facilitates the diagnosis of the pain source and reimbursement procedures as well as the ability to interface with other digital patient records, such as the Smith & Nephew digital OR system.

The report sub-system creates records of the procedure, and correlates other imaging modalities such as fluoroscopy, CT and MRI scans into the patient record. It also produces reports that have analyzed the data per protocols that have been developed by professional societies such as ISIS, NASS or reimbursing institutions. The data is in formats that can be incorporated into other digital patient record management systems such as that used by the DOD. These and other features of report sub-system 70 can be implemented by a computer readable medium including computer code.

Reports provided by sub-system 70 allow a comparison of the temporal relationship between event markers, a particular patient response, pressure and volume introduction data, and a state of fluid introduction system 20. Based on such reports, a user can discriminate between pain correlated with the onset of fluid introduction and pain more strongly correlated with a particular pressure or volume introduced. The ability to establish such temporal relationships among data acquired during a diagnostic procedure facilitates diagnostic accuracy.

Figure 11:
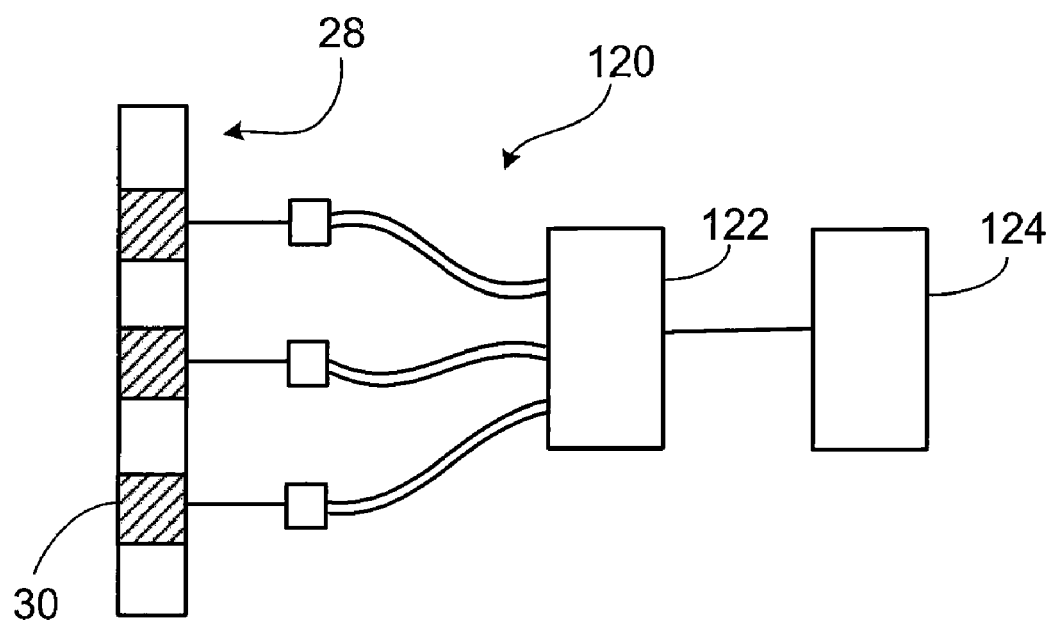
FIG. 11 is a schematic illustration of an alternative fluid introduction system.

Other embodiments are within the scope of the invention. For example, referring to FIG. 11, a fluid introduction system 120 includes an introducer 122 having at least three, e.g., at least four, fluid introduction assemblies 34 (each fluid introduction assembly is as described above) and an operator 124 to actuate the fluid introduction assemblies of introduction system 120. Embodiments of introducer 122 are described below as introducers 222 and 322.

Figure 12:
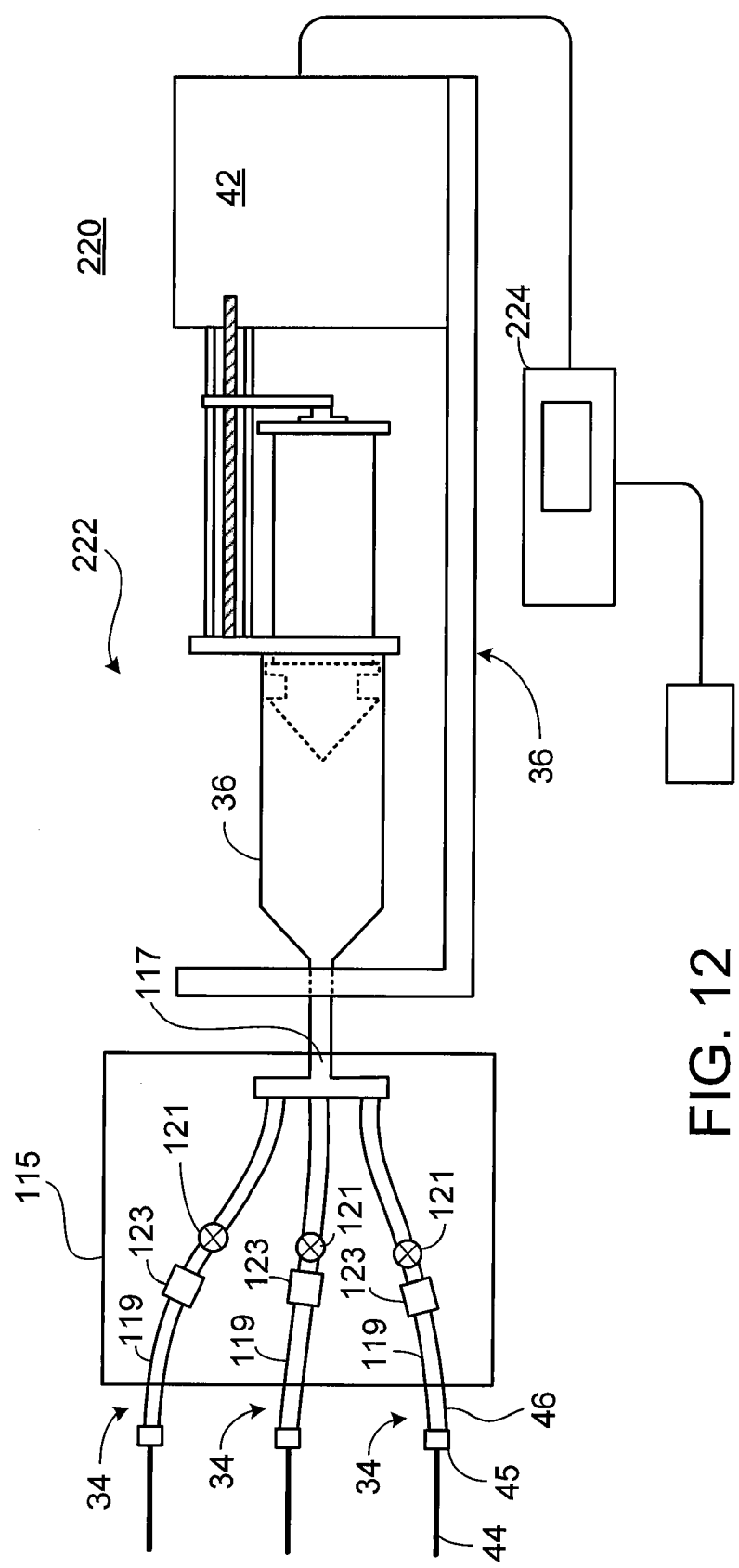
FIG. 12 is an illustration of an embodiment of the fluid introduction system of FIG. 11.

Referring to FIG. 12, a fluid introduction system 220 includes an introducer 222 having three fluid introduction assemblies 34 and a fluid drive assembly 32, as described above, coupled to each of the three fluid introduction assemblies 34 through a manifold 115. Manifold 115 defines an inflow channel 117 and three outflow channels 119. Located along each outflow channel is a valve 121 and a pressure sensor 123, which can be used as an alternative or complement to locating a pressure sensor elsewhere within introducer 222. Valves 121 control the flow of fluid from the fluid drive assembly 32 to each fluid introduction assembly 34. Operator 224 can be configured as described for operators 22 and 122. Additionally, operator 224 is in feedback communication with the valves 121 and pressure sensors 123 of manifold 115 and fluid drive assembly 32. Accordingly, operator 224 actuates valves 121 and fluid drive assembly 32 to effect predetermined fluid introduction profiles by any combination of fluid introduction assemblies 34. Operator 224 also determines the actuation of valves 121 and fluid drive assembly 32 based upon pressure readings from pressure sensors 123. Introducer 222 is preferably configured to generate a pressure in a spine of at least about 10 psi (69 kPa), 20 psi (138 kPa), 50 psi (245 kPa), 100 psi (690 kPa), 150 psi (1035 kPa), e.g., at least about 200 psi (1380 kPa) in each of at least three portions of a spine, e.g., at least four portions of a spine.

Manifold 115 allows more than one needle 44 to be connected to the syringe 36 prior to start of a fluid introduction procedure. Each needle 44 can then be positioned with respect to the spine, e.g., at an appropriate disc level or vertebral body and the valves controlled to introduce fluid sequentially or concurrently.

Figure 13:
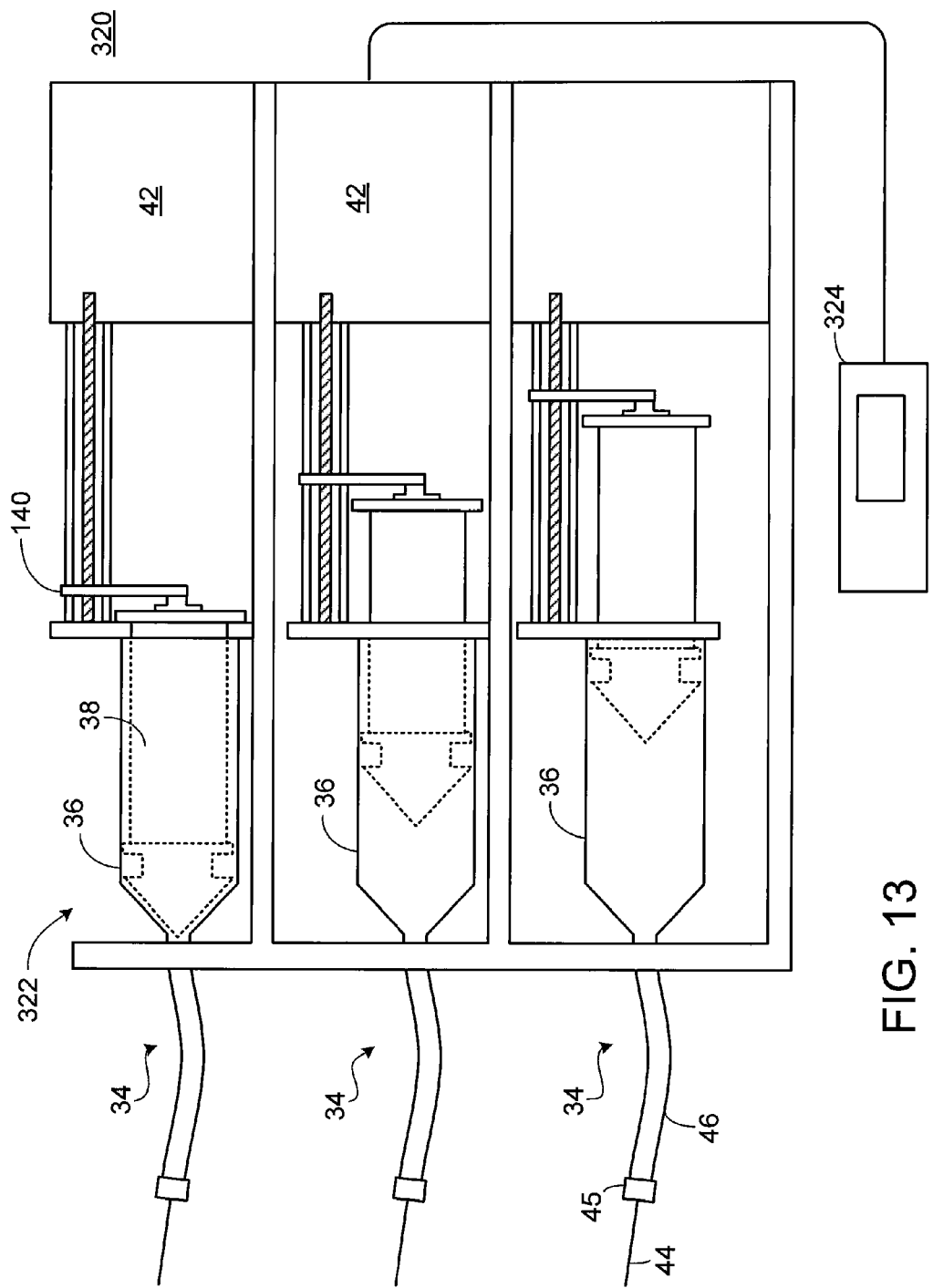
FIG. 13 is an illustration of another embodiment of the fluid introduction system of FIG. 11.

Referring to FIG. 13, a fluid introduction system 320 includes an introducer 322 having three fluid introduction assemblies 34 (each fluid introduction assembly is as described above) coupled to three fluid drive assemblies 32, as described above. Introducer 322 is preferably configured to generate a pressure in a spine of at least about 10 psi (69 kPa), 20 psi (138 kPa), 50 psi (245 kPa), 100 psi (690 kPa), 150 psi (1035 kPa), e.g., at least about 200 psi (1380 kPa) in each of at least three portions of a spine, e.g., at least four portions of a spine.

Fluid introduction systems 120, 220, and 320 allow a user to position two or more fluid introduction assemblies 34 such that each of the positioned assemblies is ready to introduce fluid into the spine, e.g., into different intervertebral discs or different vertebral bodies. Then, using the positioned assemblies, the user can introduce fluid into the spine to create a simultaneous state of pressure in each two, three, or more portions of the spine. Thus, the user can introduce fluid into two or more different portions of the spine without removing or repositioning the fluid introduction assembly from one of the portions.

Figure 14:
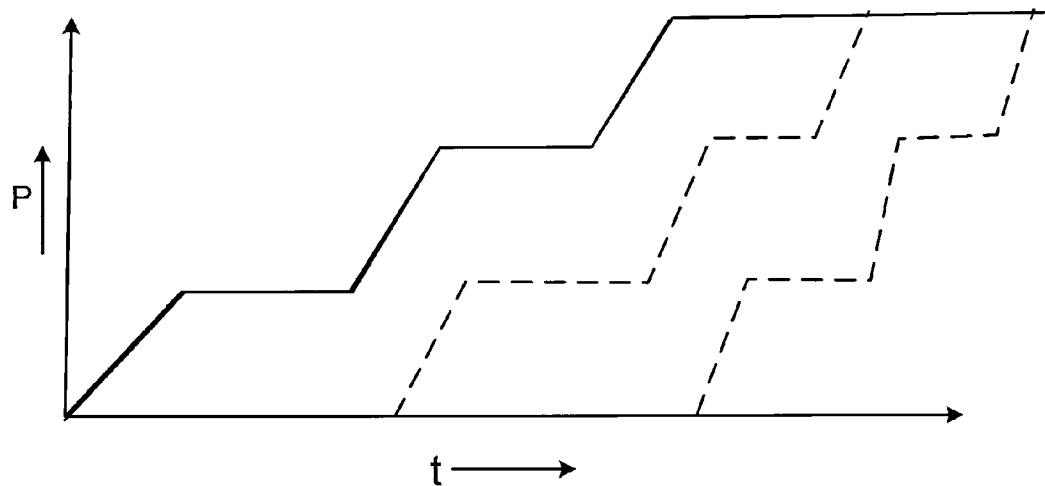
FIGS. 14 and 15 are illustrations of flow profiles.
Figure 15:
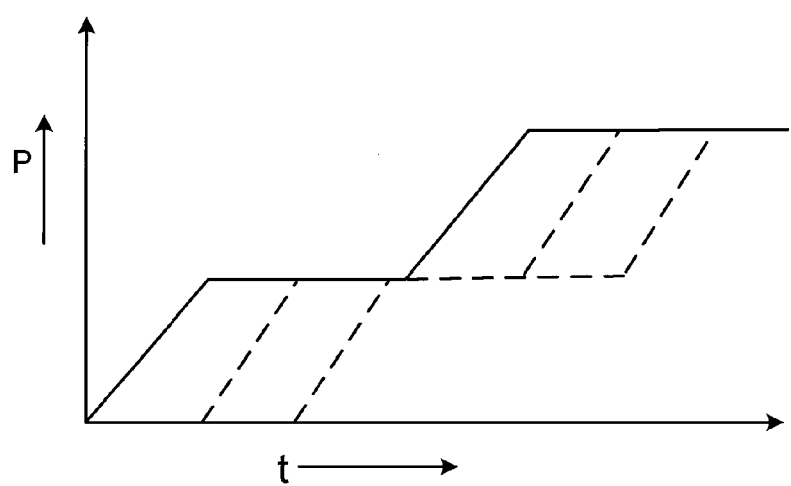

Referring to FIG. 14, using pressure or volume feedback control, the rate of increase of pressure or volume at each of three disc levels can be controlled such that each disc level is concurrently stimulated at different levels. Alternatively, as shown in FIG. 15, each disc level can sequentially be stimulated to the same level. Thus, the introduction of fluid into different portions of the spine can be concurrent, sequential, or partially overlapping in time.

What is claimed is:

1. A fluid introduction system, comprising:
    an introducer configured to introduce fluid into a spine of a patient, the introducer having a flow-rate dependent impedance opposing the introduction of the fluid and comprising a movable element disposed within the introducer, the movable element including a pressure transducer secured with respect to the movable element such that the pressure transducer is in direct contact with fluid in the introducer;
    an operator configured to actuate the introducer to introduce fluid into the spine of the patient at a constant flow rate that is not controlled by feedback based on a fluid introduction parameter and configured to determine impedance data indicative of the flow rate-dependent impedance based upon pressure and volume of fluid dispensed during an actuation of the introducer prior to insertion of the introducer into the spine;
    a computer readable medium having code that, when executed by a computer, receives:
        fluid introduction data indicative of the fluid introduction parameter;
        response data indicative of pain level of a response of the patient at a time related to a time of the fluid introduction data; and
        response data, input separately from the pain level data, indicative of concordance of the response of the patient at the time related to the time of the fluid introduction data, the concordance data indicating whether the pain level response of the patient is a result of a pain symptom or is a result of pain unrelated to the pain symptom.

2. The fluid introduction system of claim 1, wherein the fluid introduction parameter is a pressure within an intervertebral disc of the patient at the time of the fluid introduction data.

3. The fluid introduction system of claim 1, wherein the fluid introduction parameter is a total amount of fluid introduced into an intervertebral disc of the patient at the time of the fluid introduction data.

4. The fluid introduction system of claim 1, wherein the fluid introduction system is configured to obtain the response data from an observation of the patient.

5. The fluid introduction system of claim 1, wherein the fluid introduction system is configured to obtain the response data upon a response inputted by the patient.

6. The fluid introduction system of claim 1, wherein the introducer is configured to create a pressure of at least 100 kPa within the spine.

7. The fluid introduction system of claim 1, further comprising a sliding device.

8. The fluid introduction system of claim 7, wherein the response data comprises data inputted directly by the patient using the sliding device.

9. The fluid introduction system of claim 1, wherein the response data comprises observed physiological parameters.

10. The fluid introduction system of claim 1, wherein the response data is correlated with actual measurements of disc pressure and a volume of fluid introduced into one or more discs.

11. The fluid introduction system of claim 1, wherein the introducer comprises a needle configured for insertion into a spine.

12. A fluid introduction system, comprising:
    an introducer configured to introduce a non-pulsatile flow of fluid into a spine, the introducer having a flow rate-dependent impedance opposing the introduction of the fluid; and
    an operator configured to actuate the introducer, the operator including code to introduce the fluid into the spine at a constant flow rate that is not controlled by feedback based on a fluid introduction parameter and configured to empirically determine impedance data indicative of the flow rate-dependent impedance based upon pressure and volume of fluid dispensed during an actuation of the introducer prior to insertion of the introducer into the spine and to control the actuation of the introducer based at least in part upon the impedance data, wherein, using the determined impedance data, the code corrects for differences between the pressure created within the spine by the introduction of fluid and the pressure of fluid within the introducer.

13. The fluid introduction system of claim 12, wherein the introducer includes an identifier including the impedance data and the operator is configured to receive the impedance data from the identifier of the introducer.

14. The fluid introduction system of claim 12, comprising:
    a pressure sensor configured to provide pressure data indicative of a pressure of fluid present in the introducer;
    a fluid introduction sensor configured to provide fluid introduction data indicative of at least one of (a) a rate of fluid introduction and (b) an amount of fluid introduced into the portion of the spine; and wherein the operator includes code to determine the impedance data based upon the pressure data and the fluid introduction data.

15. The fluid introduction system of claim 12, wherein the introducer is configured to create a pressure of at least 69 kPa within the spine.

16. The fluid introduction system of claim 12, wherein the impedance data comprises a gauge of a fluid introduction member.

17. The fluid introduction system of claim 12, wherein the impedance data comprises a length of a fluid introduction member.

18. The fluid introduction system of claim 12, wherein the impedance data comprises an inner diameter of a fluid conduit.

19. The fluid introduction system of claim 12, wherein the impedance data comprises a length of a fluid conduit.

20. A fluid introduction system, comprising:
an introducer configured to introduce fluid into a spine of a patient, the introducer having a flow-rate dependent impedance opposing the introduction of the fluid and comprising a movable element disposed within the introducer, the movable element including a pressure transducer secured with respect to the movable element such that the pressure transducer is in direct contact with fluid in the introducer;
an operator configured to actuate the introducer to introduce fluid into the spine of the patient at a constant flow rate that is not controlled by feedback based on a fluid introduction parameter and configured to determine impedance data indicative of the flow rate-dependent impedance based upon pressure and volume of fluid dispensed during an actuation of the introducer prior to insertion of the introducer into the spine;
a computer readable medium having code that, when executed by a computer, receives:
fluid introduction data indicative of the fluid introduction parameter; and
response data indicative of pain level and concordance of a response of the patient inputted separately by hand by the patient at a time related to a time of the fluid introduction data, wherein the concordance response data indicates whether the pain level of the patient is a result of a pain symptom or is a result of pain unrelated to the pain symptom.

21. The fluid introduction system of claim 20, wherein the response data is correlated with actual measurements of disc pressure and a volume of fluid introduced into one or more discs.

22. The fluid introduction system of claim 20, further comprising a sliding device.

23. The fluid introduction system of claim 22, wherein the response data comprises data inputted directly by the patient using the sliding device.

24. The fluid introduction system of claim 22, wherein the response data is correlated with actual measurements of disc pressure and a volume of fluid introduced into one or more discs.

25. A fluid introduction system for performing discography diagnosis, comprising:
an introducer configured to introduce fluid into a spine of a patient, the introducer having a flow-rate dependent impedance opposing the introduction of the fluid and comprising a movable element disposed within the introducer, the movable element including a pressure transducer secured with respect to the movable element such that the pressure transducer is in direct contact with fluid in the introducer; and
an operator configured to actuate the introducer to introduce fluid into the spine of the patient at a constant flow rate that is not controlled by feedback based on a fluid introduction parameter and configured to determine impedance data indicative of the flow rate-dependent impedance based upon pressure and volume of fluid dispensed during an actuation of the introducer prior to insertion of the introducer into the spine;
a computer readable medium having code that, when executed by a computer, receives:
fluid introduction data indicative of the fluid introduction parameter;
pain level data of the patient responsive to the fluid introduction data; and
concordance data, input separately from the pain level data, indicating whether the pain level of the patient at a time related to the time of the fluid introduction data is a result of a pain symptom or is a result of pain unrelated to the pain symptom, wherein the discography diagnosis is based upon the correlation between the pain level and concordance data and the fluid introduction data.

26. A fluid introduction system, comprising:
an introducer configured to introduce fluid into a spine of a patient, the introducer having a flow-rate dependent impedance opposing the introduction of the fluid and comprising a syringe including a plunger slidably disposed within the syringe and a pressure transducer secured with respect to the plunger such that the pressure transducer is in direct contact with fluid in the syringe;
an operator configured to actuate the introducer to introduce fluid into the spine of the patient at a constant flow rate that is not controlled by feedback based on a fluid introduction parameter and configured to determine impedance data indicative of the flow rate-dependent impedance based upon pressure and volume of fluid dispensed during an actuation of the introducer prior to insertion of the introducer into the spine; and
a computer readable medium having code that, when executed by a computer, receives:
fluid introduction data indicative of the fluid introduction parameter; and
response data indicative of pain level and concordance of a response of the patient to the introduction of fluid, wherein the concordance response data is input separately from the pain level data and indicates whether the pain level of the patient is a result of a pain symptom or is a result of pain unrelated to the pain symptom.

27. The system of claim 26, wherein a receivable portion of the plunger is receivable within the syringe and the syringe comprises a cap secured with respect to the receivable portion of the plunger, the pressure transducer being disposed between at least a portion of the cap and at least a portion of the receivable portion of the plunger.

28. The system of 27, wherein the cap comprises a hole configured to allow fluid present within the reservoir to contact the pressure transducer.

29. The system of claim 27, wherein the cap and the plunger are not rotatable with respect to one another when the cap is secured with respect to the receivable portion of the plunger.

30. The system of claim 29, wherein the cap and the receivable portion of the plunger each comprise an asymmetrical portion, the asymmetrical portions of the cap and plunger mating with one another to secure the cap with respect to the plunger.

31. A fluid introduction system, comprising:
an introducer configured to introduce fluid into a spine of a patient, the introducer comprising a movable element disposed within the introducer, a cap defining a passage and coupled to the movable element, and a pressure transducer secured with respect to the movable element and the cap such that the pressure transducer is in direct contact with fluid in the introducer via the passage;
an operator configured to actuate the introducer to introduce fluid into the spine of the patient;
a computer readable medium having code that, when executed by a computer, receives:
fluid introduction data indicative of a fluid introduction parameter;
response data indicative of pain level of a response of the patient at a time related to a time of the fluid introduction data; and
response data, input separately from the pain level data, indicative of concordance of the response of the patient at the time related to the time of the fluid introduction data, the concordance data indicating whether the pain level response of the patient is a result of a pain symptom or is a result of pain unrelated to the pain symptom.

32. The system of claim 31, wherein the cap and the movable element are not rotatable with respect to one another when the cap is secured to the movable element.

33. The system of claim 32, wherein the cap and the movable element each comprise an asymmetrical portion, the asymmetrical portions of the cap and the movable element mating with one another to secure the cap with respect to the movable element.

34. The system of claim 31, wherein the fluid introduction parameter is a pressure within an intervertebral disc of the patient at the time of the fluid introduction data.

35. The system of claim 31, wherein the fluid introduction system is configured to obtain the response data from an observation of the patient or from a response inputted by the patient.

36. A fluid introduction system, comprising:
an introducer configured to introduce fluid into a spine of a patient, the introducer comprising a syringe including a plunger having a receivable portion slidably disposed within the syringe, the syringe comprising a cap secured with respect to the receivable portion of the plunger and a pressure transducer disposed between at least a portion of the cap and at least a portion of the receivable portion of the plunger such that the pressure transducer is in direct fluid contact with fluid in the syringe;
an operator configured to actuate the introducer to introduce fluid into the spine of the patient; and
a computer readable medium having code that, when executed by a computer, receives:
fluid introduction data indicative of a fluid introduction parameter; and
response data indicative of pain level and concordance of a response of the patient at a time related to the time of the fluid introduction data, the pain and concordance data inputted separately, wherein the concordance response data indicates whether the pain level of the patient is a result of a pain symptom or is a result of pain unrelated to the pain symptom.

37. The system of claim 36, wherein the cap and the plunger are not rotatable with respect to one another when the cap is secured to the receivable portion of the plunger.

38. The system of claim 36, wherein the cap and the receivable portion of the plunger each comprise an asymmetrical portion, the asymmetrical portions of the cap and receivable portion mating with one another to secure the cap with respect to the plunger.

39. A fluid introduction system, comprising:
an introducer configured to introduce fluid into a spine of a patient, the introducer having a flow-rate dependent impedance opposing the introduction of the fluid and comprising a syringe including a plunger slidably disposed within the syringe and a pressure transducer secured with respect to the plunger such that the pressure transducer is in direct contact with fluid in the syringe;
an operator configured to actuate the introducer to introduce fluid into the spine of the patient at a constant flow rate that is not controlled by feedback based on a fluid introduction parameter and configured to determine impedance data indicative of the flow rate-dependent impedance based upon pressure and volume of fluid dispensed during an actuation of the introducer prior to insertion of the introducer into the spine; and
a computer readable medium having code that, when executed by a computer, receives:
fluid introduction data indicative of the fluid introduction parameter; and
response data indicative of pain level and concordance of a response of the patient at a time related to the time of the fluid introduction data, wherein the concordance response data is input separately from the pain level data and indicates whether the pain level of the patient is a result of a pain symptom or is a result of pain unrelated to the pain symptom.

40. The fluid introduction system of claim 9, wherein observed physiological parameters comprise electromyographic response data.

41. The fluid introduction system of claim 9, wherein observed physiological parameters comprise audiovisual recordings of facial responses.

* * * * *

UNITED STATES PATENT AND TRADEMARK OFFICE
CERTIFICATE OF CORRECTION

| | |
|---|---|
| PATENT NO. | : 7,662,133 B2 |
| APPLICATION NO. | : 10/782900 |
| DATED | : February 16, 2010 |
| INVENTOR(S) | : Scarborough et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 424 days.

Signed and Sealed this

Twenty-eighth Day of December, 2010

David J. Kappos
*Director of the United States Patent and Trademark Office*